United States Patent [19]

Crammer et al.

[11] Patent Number: 5,064,859

[45] Date of Patent: Nov. 12, 1991

[54] LICIDAL COMPOSITIONS CONTAINING CARBOXYLIC ACIDS

[75] Inventors: Bernard Crammer; Raphael Ikan; Yani K. Mumicuoglu; Vera Weinstein, all of Jerusalem, Israel

[73] Assignees: Yissum Research Development Company of the Hebrew University of Jerusalem; Teva Pharmaceutical Industries, Inc., both of Israel

[21] Appl. No.: 284,082

[22] Filed: Dec. 14, 1988

Related U.S. Application Data

[63] Continuation-in-part of Ser. No. 146,336, Jan. 21, 1988, abandoned.

[30] Foreign Application Priority Data

Jan. 22, 1987 [IL] Israel .......................... 81350

[51] Int. Cl.$^5$ .................... A61K 31/20; A61K 31/19
[52] U.S. Cl. ........................ 514/560; 514/558; 514/572; 514/881
[58] Field of Search ............ 514/558, 560, 572, 881

[56] References Cited

U.S. PATENT DOCUMENTS

| | | | |
|---|---|---|---|
| 1,589,866 | 6/1926 | Siegler et al. | 514/558 |
| 2,396,012 | 3/1946 | Jones et al. | 514/558 |
| 4,406,884 | 9/1983 | Fawzi et al. | 514/558 |
| 4,518,593 | 5/1985 | Juvin et al. | 424/195.1 |

OTHER PUBLICATIONS

Rakel, Conn's current therapy, pp. 657-658 (1984).
The Merck Index, p. 2230, (1983).

*Primary Examiner*—Douglas W. Robinson
*Assistant Examiner*—Zohreh A. Fay
*Attorney, Agent, or Firm*—Steinberg & Raskin

[57] ABSTRACT

Licidal compositions for human use, comprising as active ingredient a compound of the formula

R—COOH  I wherein R is a straight or branched $C_8$–$C_{12}$ alkyl radical, a straight or branched $C_8$–$C_{12}$ alkenyl radical or a substituted vinyl cyclopropyl radical of formula

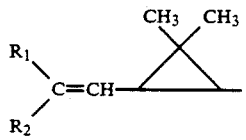

II wherein $R_1$ and $R_2$ may each be methyl, halogen or trifluoromethyl; together with a suitable carrier.

15 Claims, 3 Drawing Sheets

LICIDAL COMPOSITIONS CONTAINING CARBOXYLIC ACIDS

CROSS REFERENCE TO RELATED APPLICATION

This is a continuation in part of our copending application Ser. No. 146,336, filed Jan. 21, 1988, now abandoned.

FIELD OF THE INVENTION

The present invention relates to licidal compositions and their application to humans.

BACKGROUND OF THE INVENTION

Infestation by head lice (*Pediculus capitis*) has become a worldwide problem and has been steadily increasing during the past three decades. Head lice are a very serious problem in Israel with at least 30% infestation, particularly of young school children.

There are a number of commercial insecticides such as allethrin, pyrethrum, malathion and carbaryl that are quite effective as licides but not very effective as ovicides to lice eggs. Carbaryl has been the most effective provided this insecticide is applied to the infected region for about twelve hours. Further there are a number of side effects which have been recorded for this carbamate and include nausea, vomiting, diarrhea, blurred vision, cyanosis, convulsions and coma.

According to the U.S. National Institute for Occupational Safety and Health (NIOSH), there are indications that Carbaryl (1-naphthyl-N-methylcarbamate), is carcinogenic in animals. It has now been found that the highly effective pyrethroids such as permethrin resmethrin and natural pyrethrins are becoming less effective to the house fly, horn fly and mosquitoes [Golenda & Forgash, J. Econ. Entomol., 78, 19 (1985); Schmidt et al., ibid, 78, 402 (1985); Scott & Georghiou, ibid, 78, 316 (1985)]. It is known that the pyrethroids are not stable in air and light and gradually lose their activity within a short time. Malathion has also been found to be less effective to a number of insects and is limited in its use to animals and man.

It has been disclosed by McFarlane & Henneberry [Comp. Biochem. Physiol., 24, 377 (1968)] that $C_{12}$ fatty acids, among others, inhibit the growth of crickets. It has been found that $C_8$-$C_{11}$ fatty acids, such as undecanoic acid, are effective insecticides to beetles, *Calandra oryzae* [Ikan, Shaaya and Grossman, Israel J. Entomology, XI, 81, 1976]. These fatty acids are also useful for protecting store products, such as wheat, as they are effective insecticides to certain beetles such as Callosobruchus chinensis and *Calandra oryzae* [Israel Patent No. 53570]. These fatty acids also act as effective larvicides to the housefly (*Musca domestica*) [Quraishi & Thorsteinson, J. Econ. Entomol., 58, 400 (1965)]; *Tribolium confusum* [House & Graham, Can. Entomol., 99, 994, (1967)] and mosquito larvae [Can. Entomol., 103, 1435 (1971)].

It has been disclosed that octanoic acid has ovicidal activity to the eggs of Aedes aegypti, [J. Econ. Entomol, 65(1), 177 (1972)].

Recently $C_2$ to $C_8$ carboxylic acids have been mentioned in U.S. Pat. No. 4,518,593 as active ingredients in insecticidal compositions for use in shampoos against lice and fleas. Only acetic acid was used in the examples and specifically claimed. Surprisingly this disclosure clearly states that upon replacing acetic acid by propionic acid or caprylic acid the results were substantially inferior to acetic acid.

U.S. Pat. No. 1,589,866 relates to the use of fatty acids as insecticides to destroy plant parasites and fungi. The patent does not mention licidal activity or application to any species of the Anaplura and in particular *Pediculus capitis*.

U.S. Pat. No. 2,396,012 relates to compositions used as insect repellents, these compositions containing active antimicrobial agents, one of the agents mentioned being n-capric acid. The patent does not mention any possible specific licidal and ovicidal activity of the agents mentioned therein.

U.S. Pat. No. 4,406,884 relates to antimicrobial compositions containing $C_5$-$C_{12}$ fatty acids in the treatment of skin disorders. There is no mention in the patent of any possible licidal effect of the acids and none of the skin disorders mentioned therein relate to lice infestation.

An article by Robert E. Rakel in Conn's Current Therapy, 1984, pages 657-658, teaches the use of shampoos containing certain specific insecticides for the treatment of lice. The insecticides mentioned are known licidal agents, namely Lindane (gamma-benzene hexachloride), Crotamiton, Pyrethrins and Malathion. There is no mention in this reference of the use of any fatty acids as licidal shampoos.

SUMMARY OF THE INVENTION

Surprisingly certain carboxylic acids such as capric acid, undecanoic acid, undecenoic acid and trans chrysanthemic acid have been found to be effective as insecticides to human head lice and their eggs. These fatty acids, except trans chrysanthemic acid, are not only very stable but are the least toxic compared to the commercially available insecticides which are used as licides. Furthermore, these carboxylic acids are inexpensive to produce and thus afford a further important advantage over licides already on the market.

Accordingly, the invention provides a licidal composition characterized in that it comprises up to 30% by weight or more as active ingredient a compound of the formula

R—COOH    I wherein R is a straight or branched $C_8$-$C_{12}$ alkyl radical, a straight or branched $C_8$-$C_{12}$ alkenyl radical or a substituted vinylcyclopropanyl radical of the formula

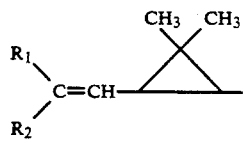

wherein $R_1$ and $R_2$ may each be methyl halogen or trifluoromethyl; together with a suitable carrier.

The novel licidal compositions according to the invention are suitable for human use.

Preferred compositions according to the invention are those in which the moiety R of the said active ingredient of formula I above is a $C_9$-$C_{12}$ alkyl radical, particularly $C_{10}$-$C_{12}$. Another of preferred compositions are those in which the moiety R of the said active ingredient of formula I above is a radical of formula II above, examples of such acids being cis chrysanthemic acid $R_1=R_2=CH_3$, or cis or trans permethric acid $R_1=R_2=Cl$.

The carboxylic acids used in accordance with the invention have been found to be not only very effective in killing lice but also and even more effective in killing their eggs as well.

The licidal composition according to the present invention may contain more than one active ingredient of a carboxylic acid as hereinbefore defined, preferably in an amount of up to 30% by weight. For example, a licidal composition may contain up to 30% by weight as active ingredients of a 1:1 mixture of capric acid and trans permethric acid.

The invention further provides a method of combating lice in humans which comprises applying a licidally effective amount of a carboxylic acid of formula I to the area to be treated.

The said carboxylic acids are in general readily soluble in organic solvents making liquid formulations very simple, and the resulting compositions easy to handle.

For the purpose of the present invention, a carrier may be any material capable of facilitating application to an area of a human to be treated and adapted to facilitate storage, transportation or handling. The carrier may be solid or liquid as well as a liquified gas. It is possible to employ for the purposes of the present invention any of the carriers normally used in the formulation of pesticidal compositions for human use provided it is compatible with the said active ingredient.

Suitable solid carriers include natural and synthetic clays and silicates, for example natural silicates such as diatomaceous earths; magnesium silicates, for example talcs, magnesium aluminum silicates, for example, attapulgites and vermiculites; aluminum silicates, for example kaolinites, montmorillonites and micas; calcium carbonate; calcium sulphate; synthetic hydrated silicon oxides and synthetic calcium or aluminum silicates; native elements such as, for example, carbon and sulphur; natural and synthetic resins, for example coumarone resins, polyvinyl chloride, and styrene polymers and copolymers.

Suitable liquid carriers include water, ketones, for example, acetone, methyl ethyl ketone, methyl isobutyl ketone and cyclohexanone; ethers, for example, diethyl ether, ethyl propyl ether and di-isopropyl ether; alcohols, for example, ethanol, propanol, isopropanol, isobutanol, and glycols such as ethylene glycol.

The compositions of the invention may for example be formulated as wettable powders, dusts, granules, solutions, lotions, emulsifiable concentrates, emulsions, suspension concentrates, aerosols, soaps and shampoos. Wettable powders may contain up to 75% by weight of active ingredient and usually contain, in addition to solid inert carrier, 3-10% by weight of a dispersing agent and, if desired, up to 10% by weight of a stabilizer and/or other additivies such as penetrants and stickers. Dusts are usually formulated as a dust concentrate having similar compositions to that of a wettable powder but without dispersant, and are diluted, prior to use, with a further solid carrier to yield compositions usually containing up to 10% by weight of active ingredient. Granules are usually prepared to have a size between 10 and 100.BS mesh [1.67-0.15 mm], and may be manufactured by agglomeration or impregnation techniques. Usually, granules will contain up to 25% by weight of active ingredient and 0-10% by weight of additives such as stabilizers, slow release modifiers and binding agents.

Emulsifiable concentrates often contain, in addition to a solvent and, when necessary, co-solvent, 10-50% w/v active ingredient, 2-20% w/v emulsifiers and 0-20% w/v of other additives such as stabilizers, penetrants and corrosion inhibitors. Suspension concentrates are usually compounded so as to obtain a stable non-sedimenting flowable product and usually contain 5-80% by weight active ingredient, 0.5-15% by weight of dispersing agents, 0.1-10% by weight of suspending agents such as protective colloids and thixotropic agents 0-10% by weight of other additives such as defoamers, corrosion inhibitors, stabilizers, penetrants and stickers and water or an organic liquid in which the active ingredient is substantially insoluble; certain organic solids or inorganic salts may be present dissolved in the formulation to assist in preventing sedimentation or as anti-freeze agents for water.

Formulations preferably containing up to 30% by weight of active ingredient, more preferably about 2-30%, according to the invention may be used on humans. For the treatment of human hair against lice, liquid formulations have been found suitable, e.g. agents that contain up to 20% by weight of active ingredient, preferably between 3 and 5% by weight in an alcohol and water mixture.

Other suitable formulations may include shampoos and soaps. Such shampoos may include 10 to 30% active ingredient, ammonium lauryl sulphate, an alkylene glycol such as for example propylene glycol, an alkaline salt of EDTA such as for example the disodium salt of EDTA, formaldehyde and a 2-halo-2-nitropropane-1,3-diol such as for example 2-bromo-2-nitropropane-1,3-diol. Suitable soaps are the alkali metal salts, alkaline earth metal salts or unsubstituted ammonium salts of one of the active ingredients such as for example capric acid, undecanoic acid, undecenoic acid or trans chrysanthemic acid either individually or a mixture with one of the higher fatty acids such as the sodium or potassium salt of oleic or stearic acid or of fatty acid mixtures which can be obtained e.g. from coconut oil or tallow oil.

Application of compositions containing the active ingredient of the present invention to an area of a human infested with lice, generally human hair, results in a high degree of licidal activity and is most effective. The use of these agents is particulary effective in that the same are not only effective against the lice but also their eggs.

DESCRIPTION OF PREFERRED EMBODIMENTS

For better understanding there now follow an experimental part with test results for some liquid formulations according to the invention containing as active ingredient a carboxylic acid of the formula R—COOH where R represents capric acid, undecanoic acid, undecenoic acid and trans chrysanthemic acid on body lice (*Pediculus humanus*). It should however, be understood that these specific embodiments are only representative examples of the invention as hereinbefore described. Further such formulations may be applied to any member of the sub-order Anoplura particularly of the Pediculidae and linognathidae families.

LICE COLONIES

Laboratory colonies of body lice (*Pediculus humanus*) were maintained at 20°±2° C. and at 70-80% humidity. Every second day, the lice were placed on the shaved abdomen of a restrained rabbit and were allowed to feed until satiated. The lice used in the experiments received a blood meal two to four hours before treatment.

LICIDAL FORMULATIONS

60% ethanol/water mixtures containing 1%, 3% and 5% carboxylic acids selected from capric acid, undecanoic acid, undecenoic acid and trans chrysanthemic acid were prepared.

TEST METHOD 50 specimens of *Pediculus humanus* (10 males, 10 females and 30 nymphs at different development stages) were placed on a white filter paper (7 cms diameter) and 1 ml of the formulation containing one of the active ingredients was added. The lice remained in contact for 10, 15, 20, 30 minutes, 2 hours and 4 hours and then washed for one minute with water.

The lice were then transferred to a filter paper and placed in an incubator for 24 hours at 29° C. and 70–80% relative humidity. The number of lice surviving were counted. Each experiment was repeated three times and for each experiment a control test was also carried out using 50 lice. A 60% ethanol/water mixture was used in the control tests.

TEST METHOD FOR OVICIDAL ACTIVITY

Lice (*Pediculus humanus*) were placed on human hair and were allowed to oviposite for 48 hours. 50 eggs (2–6 days old) were treated in the same way as the lice except that the incubation period was for 10 minutes. The mortality rate was determined after ten days.

Figure 1:
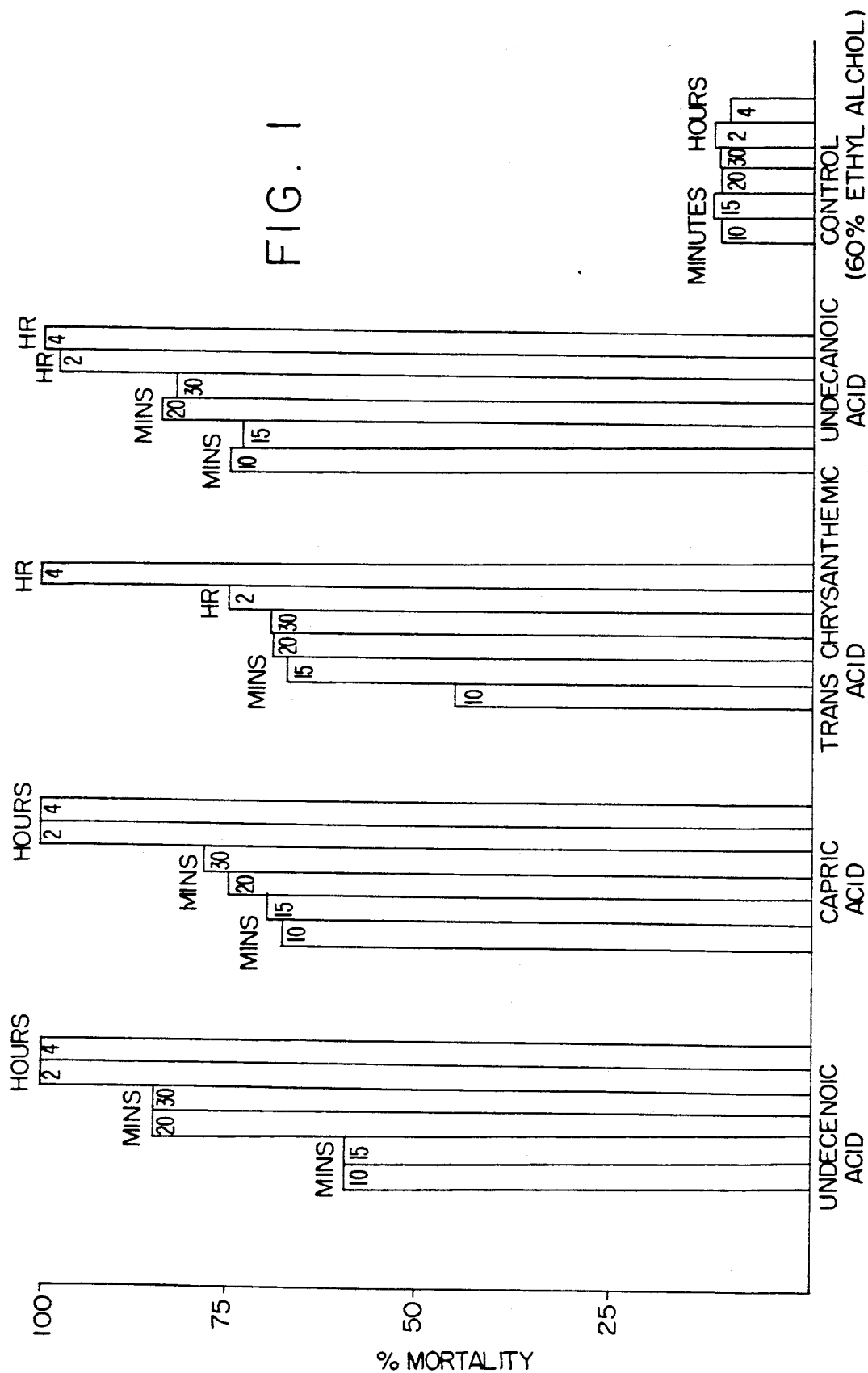
Figure 2:
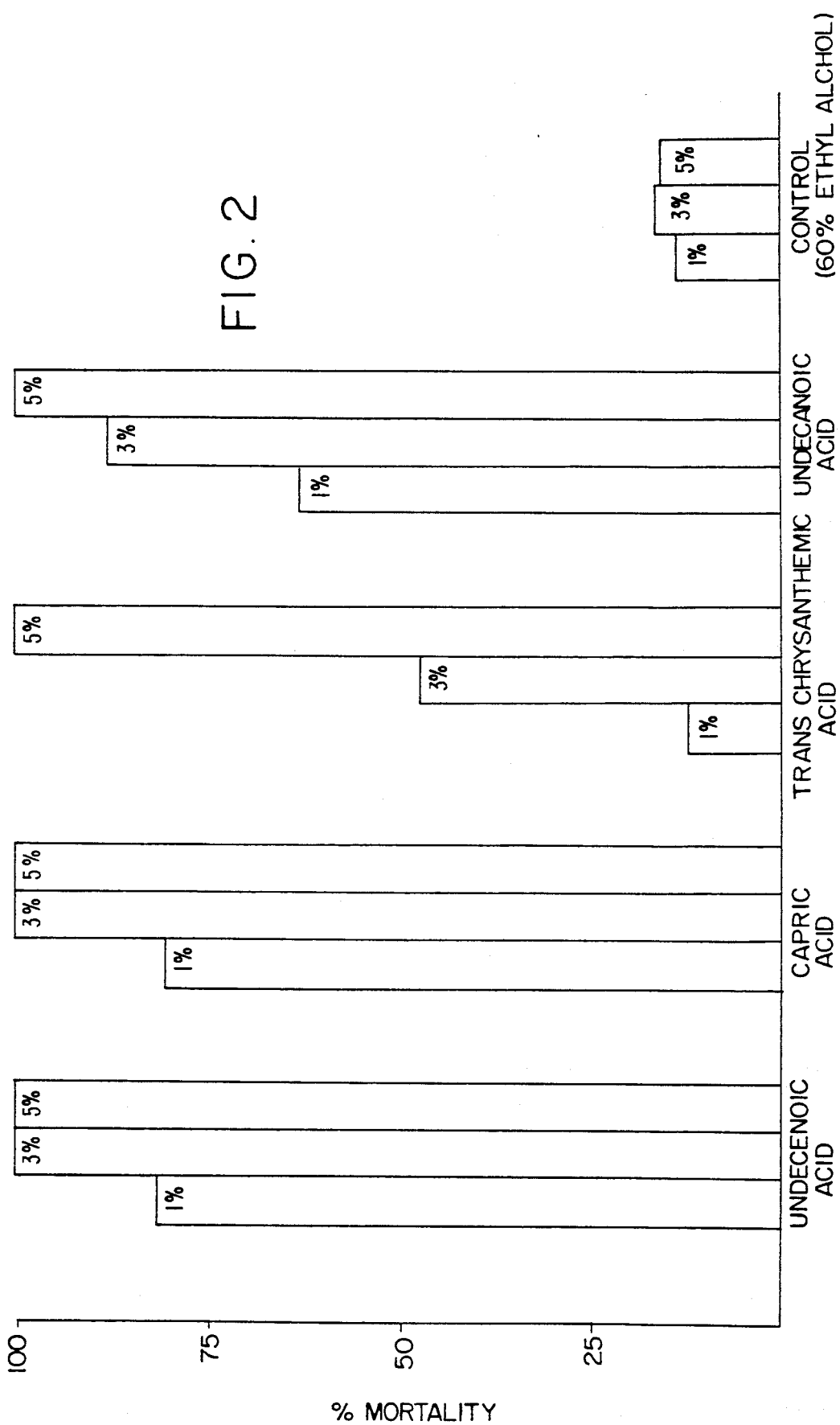
Figure 3:
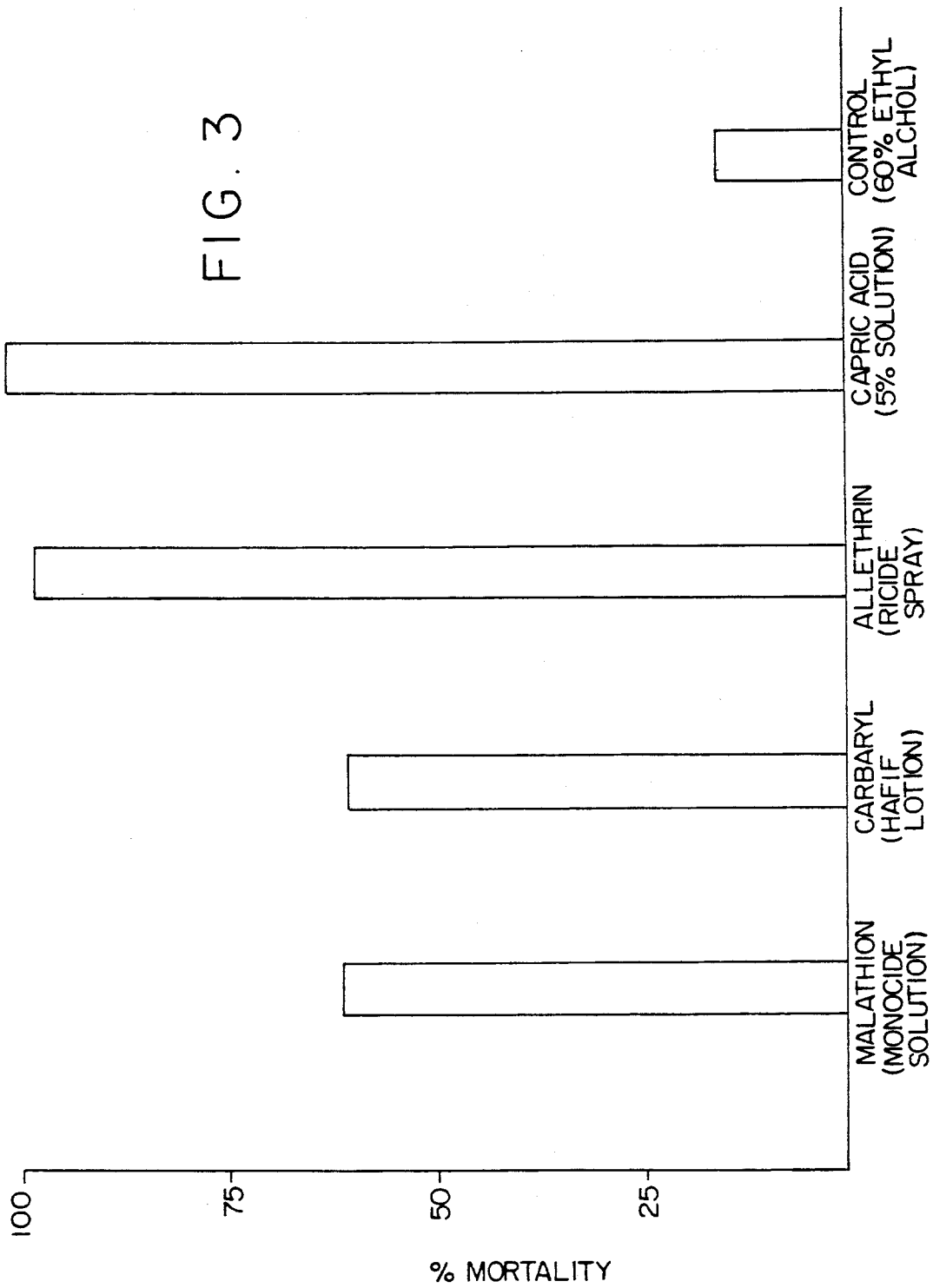

In the following test results reference will be had to the annexed drawings in which:

FIG. 1 illustrates the licidal activity of 5% solutions according to the invention after different periods of exposure;

FIG. 2 illustrates the ovicidal activity of 1%, 2% and 3% solutions according to the invention after 10 minute exposure; and FIG. 3 illustrates the ovicidal activity of some 5% prior art solutions and a solution according to the invention after 10 minutes exposure.

RESULTS

(i) Lice

Using a 5% solution it was found that undecanoic and capric acids caused 100% mortality after an incubation time of two hours. Undecanoic and trans chrysanthemic acids were 100% effective after four hours. Control with the solvent gave about 10% mortality (FIG. 1).

(ii) Eggs

An exposure time of ten minutes was sufficient to cause 100% mortality of the lice eggs using a 5% solution of the carboxylic acid. Undecenoic and capric acids were 100% effective after ten minutes contact time with a 3% solution. Control with the 60% ethanol/water mixture gave only 12–14% mortality (FIG. 2).

It was further found that a 5% solution of capric acid was the most effective ovicide to lice eggs compared to the known formulations on the market (FIG. 3).

The results show that the formulations containing an active ingredient according to the invention were excellent ovicides and licides.

For further illustration there now follow examples of formulations according to the invention. The formulations are prepared by conventional procedures known to those skilled in the art.

EXAMPLE 1

Nonionic Lotion—pH 5.1

| Phase A | |
|---|---|
| Methyl Glucose Sesquistearate | 0.5% |
| Methyl Gluceth-20 Sesquistearate | 1.5% |
| Cetyl Alcohol | 0.5% |
| Capric acid | 5.0% |
| Isopropyl Lanolate | 0.5% |
| Phase B | |
| Carbomer 934 [4% Aqueous dispersion] | 7.5% |
| Germaben II [Sutton: Propylene Glycol, diazolidinyl Urea, Mehyl Paraben and Propyl Paraben] | 1.0% |
| Triethanolamine, 99% | 0.3 |
| Water | 83.2% |
| | 100.0 |

EXAMPLE 2

Clear Shampoo—pH 4.8

| Phase A | |
|---|---|
| Triethanolamine, 99% | 4.0% |
| Standapol A (28% Ammonium Lauryl Sulphate) | 30.0% |
| Water | 28.55% |
| Phase B | |
| Surfine AZI-A [Nonoxynol-10 Carboxylic Acid] | 20.0% |
| Propylene Glycol, USP | 12.0% |
| Capric Acid | 5.0% |
| Phase C | |
| Clydant [DMDM Hydantoin] | 0.2% |
| Perfume [Fragrance Resources #86F904] | 0.25% |
| | 100.00 |

EXAMPLE 3

| | |
|---|---|
| Klucel HF (hydroxypropylcellulose) | 0.8% |
| Propylene Glycol | 5.0% |
| SD40 Ethanol (95%) | 84.0% |
| Capric Acid | 10.0% |
| Fragrance and Color | 0.2% |
| | 100.00 |

MANUFACTURE

Disperse Klucel into alcohol, then add rest of ingredients. Heat to melt Capric acid if necessary.

EXAMPLE 4

| Phase A | |
|---|---|
| Water | 54.2% |
| Carbopol | 0.8% |
| Phase B | |
| Propylene Glycol | 5.0% |
| SD40 Ethanol (95%) | 30.0% |
| Tween 20 | 3.0% |
| Capric Acid | 5.0% |
| Triethanolamine | 2.0% |
| | 100.00 |

MANUFACTURE a) Disperse Carbopol in Water first.

b) Melt Capric acid into the Alcohol, Propylene Glycol, Tween 20 and Triethanolamine. (Heat slightly if necessary).

c) Slowly add Phase A to Phase B, via high speed propellor agitation.

EXAMPLE 5

| Combination of Syndat/Soap Bar | |
|---|---|
| Tetronic 1508 (Polyamine 1508) | 18.0% |
| Pluracol E 4000 (PEG-75) | 10.0% |
| Soap (20 Coc, 80 Tallow) | 40.0% |
| Hydrogenated Peanut Oil | 10.0% |
| Capric Acid | 5.0% |
| Sodium Lauroylisethionate | 5.4% |
| Stearic Acid TP | 5.0% |
| Hydrogenated Cottonseed Oil | 5.0% |
| Titanium Dioxide | 1.0% |
| Perfume/Antioxidant etc. | 0.6% |
| | 100.00 |

PROCEDURE

Mix all ingredients in a suitable container. Pass over a 9-5oll mill and convert into ribbons. Feed ribbons to a double vacuum plodder and extrude at 140°–150° F. Cut and press in suitable equipment. Mill and plodder may require more power than similar equipment used for soap.

EXAMPLE 6

| Soap Bar | |
|---|---|
| Tallow/Coconut Soap (80/20%) | 95.0% |
| Capric Acid | 5.0% |
| Perfume and Color | q.s |
| | 100.0 |

PROCEDURE

Weigh and add the soap base into a suitable blender. (A ribbon blender is suggested.) Begin mixing while weighing in the other ingredients. Continue stirring until the blend is completely homogeneous. Continue processing the formulation by either milling or passing through refiner-plodders. Press into desired cakes and wrap.

While the invention has been described with respect to particular compositions, it is apparent that variations and modifications of the invention can be made without departing from the spirit of scope thereof.

What is claimed is:

1. A method of combatting lice in humans, which comprising applying to an area of a human infested with lice a licidal effective amount of carboxylic acid of the formula $$R-COOH \qquad I$$

wherein R is a straight or branched $C_8$–$C_{12}$ alkyl radical, a straight or branched $C_8$–$C_{12}$ alkenyl radical or a substituted vinylcyclopropanyl radical of the formula

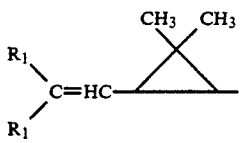

wherein $R_1$ and $R_2$ may each be methyl, halogen or trifluoromethyl.

2. The method according to claim 1 wherein said carboxylic acid is present in an amount of about 1–30% by weight.

3. The method according to claim 1 wherein R is a straight or branched $C_9$–$C_{12}$ alkyl group.

4. The method according to claim 1 wherein R is a straight or branched $C_{10}$–$C_{12}$ alkyl group.

5. The method according to claim 1 wherein said carboxylic acid is capric acid, undecanoic acid or undecenoic acid.

6. The method according to claim 1 wherein said carboxylic acid is chrysanthemic acid or permethric acid.

7. The method according to claim 1 wherein said carboxylic acid is applied in a carrier which is liquid and wherein said compound is present in said carrier in an amount of 1 to 20% by weight.

8. The method according to claim 7 wherein said carboxylic acid is present in an amount of about 3–5% by weight.

9. The method according to claim 1 wherein said carboxylic acid is applied in the form of a composition containing between about 2 and 20% by weight of said carboxylic acid.

10. The method according to claim 9 wherein said composition contains 3–5% by weight of said carboxylic acid in an aqueous alcohol formulation containing 3% or 5% alcohol.

11. The method according to claim 1 wherein said carboxylic acid is dispersed in a shampoo base and is applied to the infested area as a shampoo.

12. The method according to claim 1 wherein said carboxylic acid is dispersed and applied to the infested area as a soap.

13. The method of claim 1, wherein $R_1=R_2=CH_3$.

14. The method of claim 1, wherein $R_1=R_2=Cl$.

15. The method of claim 1, comprising applying a 1:1 mixture of captric acid and trans permethric acid.

* * * * *